(12) United States Patent
High et al.

(10) Patent No.: US 9,075,044 B2
(45) Date of Patent: Jul. 7, 2015

(54) COMPOSITIONS AND METHODS FOR DETECTION AND MODULATION OF T CELL MEDIATED IMMUNE RESPONSES AGAINST VIRAL VECTORS UTILIZED FOR GENE THERAPY

(75) Inventors: Katherine A. High, Merion, PA (US); Marcela V. Maus, New York, NY (US); Federico Mingozzi, Philadelphia, PA (US); Daniel J. Hui, Chesterbrook, PA (US)

(73) Assignee: THE CHILDREN'S HOSPITAL OF PHILADELPHIA, Philadelphia, PA (US)

( * ) Notice: Subject to any disclaimer, the term of this patent is extended or adjusted under 35 U.S.C. 154(b) by 959 days.

(21) Appl. No.: 12/302,206

(22) PCT Filed: May 31, 2007

(86) PCT No.: PCT/US2007/070147
§ 371 (c)(1),
(2), (4) Date: Oct. 15, 2009

(87) PCT Pub. No.: WO2007/140474
PCT Pub. Date: Dec. 6, 2007

(65) Prior Publication Data
US 2010/0035806 A1 Feb. 11, 2010

Related U.S. Application Data

(60) Provisional application No. 60/809,956, filed on May 31, 2006.

(51) Int. Cl.
| | |
|---|---|
| C07K 7/06 | (2006.01) |
| G01N 33/50 | (2006.01) |
| C07K 14/725 | (2006.01) |
| A61K 38/00 | (2006.01) |

(52) U.S. Cl.
CPC .......... *G01N 33/505* (2013.01); *C07K 14/7051* (2013.01); *C12N 2750/14143* (2013.01); *G01N 2333/015* (2013.01); *A61K 38/00* (2013.01)

(58) Field of Classification Search
None
See application file for complete search history.

(56) References Cited

U.S. PATENT DOCUMENTS

2005/0003484 A1   1/2005   Hirano et al.
2005/0112576 A1   5/2005   Deml et al.

OTHER PUBLICATIONS

Chen et al., Molecular Therapy vol. 13, No. 2, Feb. 2006, pp. 260-269.*
Mingozzi et al., Nature Medicine, vol. 13, No. 4, 2007, pp. 419-422 and Supplemental pp. 1-15.*
Goldsby et al., "Immunology," 5th ed., W.H. Freeman and Co., 2002, pp. 170-171.*
Mingozzi et al., Current Gene Therapy, 2011, 11, 321-330, p. 325, left col., "Leading . . .".*
Memorandum from Deputy Commissioner for Patent Examination Policy Andrew H. Hirshfeld, dated Mar. 4, 2014, pp. 1-19.*
Evaluating subject Matter Eligibility Under 35 U.S.C. § 101, Mar. 19, 2014 update, pp. 1-93.*
Wooldridge et al. (J. Biol. Chem. 2012, 287:1168-1177).*
Persuad et al. (Nature Immunology 15, 266-274 (2014)).*
Martin et al. (Nature Immunology 15, 217-219 (2014)).*
Chirmule, et al. "Immune responses to adenovirus and adeno-associated virus in humans." Gene Therapy, 6(9): 1574-1583 (Sep. 1999).
Laugel, et al. "Design of Soluble Recombinant T Cell Receptors for Antigen Targeting and T Cell Inhibition." Journal of Biomedical Chemistry, 280(3): 1182-1892 (Jan. 21, 2005).
Hauck, B., et al. "Intracellular viral processing, not single-stranded DNA accumulation, is crucial for recombinant adeno-associated virus transduction." J Virol. Dec. 2004;78(24):13678-86.
Manno, C.S., et al. "Successful transduction of liver in hemophilia by AAV-Factor IX and limitations imposed by the host immune response." Nat Med. Mar. 2006;12(3):342-7. Epub Feb. 12, 2006.
"MHC class I molecules bind short peptides of 8-10 amino acids by both ends." In Janeway's Immunobiology, 7th Edition, Kenneth Murphy, et al., eds. Nov. 27, 2007. Garland Science: New York.
Sabatino, D.E., et al. "Identification of mouse AAV capsid-specific CD8+ T cell epitopes." Mol Ther. Dec. 2005;12 (6):1023-33. Epub Nov. 2, 2005.

* cited by examiner

*Primary Examiner* — Zachary Skelding
(74) *Attorney, Agent, or Firm* — Kathleen D. Rigaut; Robert C. Netter, Jr.; Dann, Dorfman, Herrell & Skillman

(57) ABSTRACT

Compositions and methods are provided for inhibiting T cell mediated destruction of virally transduced, trangene containing cells.

5 Claims, 12 Drawing Sheets

Figure 3

Peptide 74 (366-380)

Figure 1:
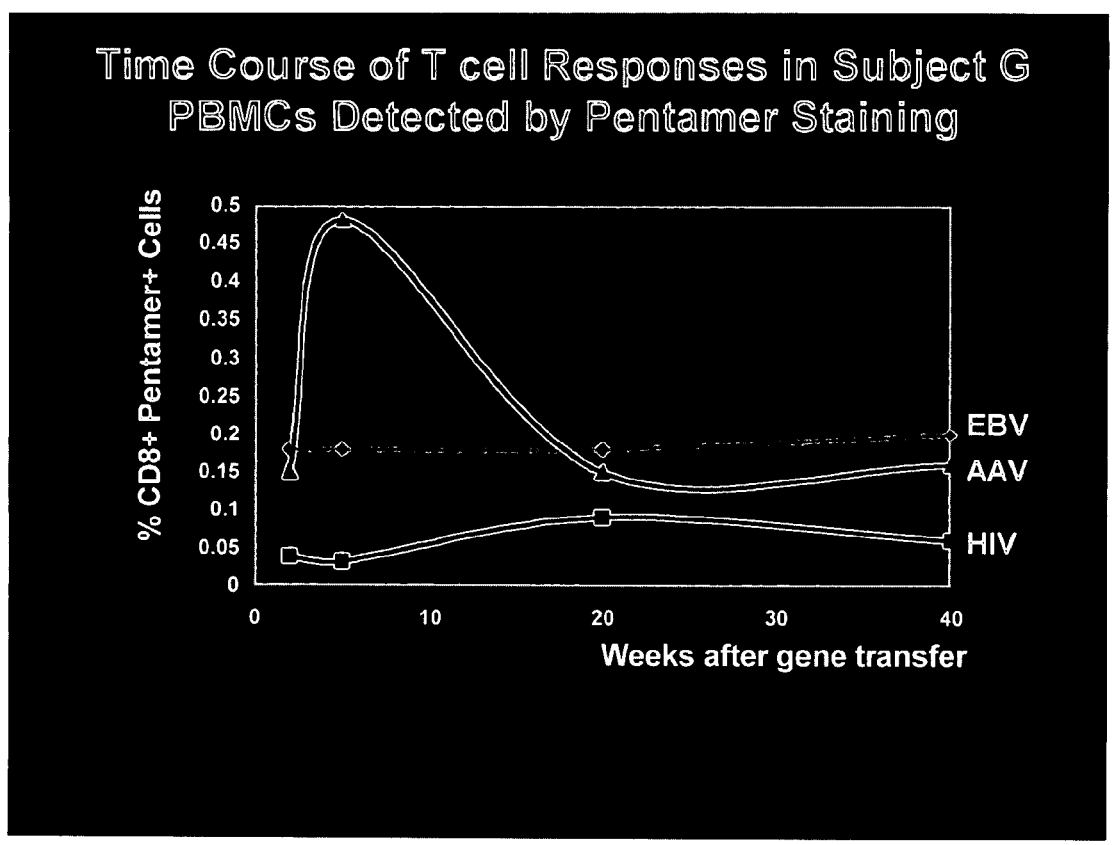

| | | | |
|---|---|---|---|
| AAV-1 | VP1 | (340) | TVQVFSDSEYQLPYVLGSAHQGCLPPF*PADVFMIPQYGYLTLNNGSQ*--- |
| AAV-2 | VP1 | (339) | TVQVFTDSEYQLPYVLGSAHQGCLPPF*PADVFMVPQYGYLTLNNGSQ*--- |
| AAV-3a | VP1 | (339) | TVQVFTDSEYQLPYVLGSAHQGCLPPF*PADVFMVPQYGYLTLNNGSQ*--- |
| AAV-3b | VP1 | (339) | TVQVFTDSEYQLPYVLGSAHQGCLPPF*PADVFMVPQYGYLTLNNGSQ*--- |
| AAV-4 | VP1 | (330) | TVQIFADSSYELPYVMDAGQEGSLPPF*PNDVFMVPQYGYCGLVTGNTSQQ* |
| AAV-5 | VP1 | (330) | TVQVFTDDDYQLPYVVGNGTEGCLPAF*PPQVFTLPQYGYATLNRDNTEN*- |
| AAV-6 | VP1 | (340) | TVQVFSDSEYQLPYVLGSAHQGCLPPF*PADVFMIPQYGYLTLNNGSQ*--- |
| AAV-7 | VP1 | (341) | TIQVFSDSEYQLPYVLGSAHQGCLPPF*PADVFMIPQYGYLTLNNGSQ*--- |
| AAV-8 | VP1 | (342) | TIQVFTDSEYQLPYVLGSAHQGCLPPF*PADVFMIPQYGYLTLNNGSQ*--- |

Peptide 82 (406-420)

| | | | |
|---|---|---|---|
| AAV-1 | VP1 | (387) | AVGRSSFYCLEYFPSQMLRT*GNNFTFSYTFEEVPFHSSYAHSQSLDRLMN* |
| AAV-2 | VP1 | (386) | AVGRSSFYCLEYFPSQMLRT*GNNFTFSYTFEDVPFHSSYAHSQSLDRLMN* |
| AAV-3a | VP1 | (386) | AVGRSSFYCLEYFPSQMLRT*GNNFQFSYTFEDVPFHSSYAHSQSLDRLMN* |
| AAV-3b | VP1 | (386) | AVGRSSFYCLEYFPSQMLRT*GNNFQFSYTFEDVPFHSSYAHSQSLDRLMN* |
| AAV-4 | VP1 | (380) | QTDRNAFYCLEYFPSQMLRT*GNNFEITYSFEKVPFHSMYAHSQSLDRLMN* |
| AAV-5 | VP1 | (379) | PTERSSFFCLEYFPSKMLRT*GNNFEFTYNFEEVPFHSSFAPSQNLFKLAN* |
| AAV-6 | VP1 | (387) | AVGRSSFYCLEYFPSQMLRT*GNNFTFSYTFEDVPFHSSYAHSQSLDRLMN* |
| AAV-7 | VP1 | (388) | SVGRSSFYCLEYFPSQMLRT*GNNFEFSYSFEDVPFHSSYAHSQSLDRLMN* |
| AAV-8 | VP1 | (389) | AVGRSSFYCLEYFPSQMLRT*GNNFQFTYTFEDVPFHSSYAHSQSLDRLMN* |

FIG. 5A
Clone a-TCRα-AV17AJ43 (SEQ ID NO: 19)

ATGGAAACTCTCCTGGGAGTGTCTTTGGTGATTCTATGGCTTCAACTGGCT
AGGGTGAACAGTCAACAGGGAGAAGAGGATCCTCAGGCCTTGAGCATCC
AGGAGGGTGAAAATGCCACCATGAACTGCAGTTACAAAACTAGTATAAAC
AATTTACAGTGGTATAGACAAAATTCAGGTAGAGGCCTTGTCCACCTAAT
TTTAATACGTTCAAATGAAAGAGAGAAACACAGTGGAAGATTAAGAGTCA
CGCTTGACACTTCCAAGAAAAGCAGTTCCTTGTTGATCACGGCTTCCCGGG
CAGCAGACACTGCTTCTTACTTCTGTGCTACGGACCCCCGTACAATAACA
ATGACATGCGCTTTGGAGCAGGGACCAGACTGACAGTAAAACCAAATATC
CAGAACCCTGAC

FIG. 5B
Clone a-TCRα-AV17AJ31 (SEQ ID NO: 20)

ATGGAAACTCTCCTGGGAGTGTCTTTGGTGATTCTATGGCTTCAACTGGCT
AGGGTGAACAGTCAACAGGGAGAAGAGGATCCTCAGGCCTTGAGCATCC
AGGAGGGTGAAAATGCCACCATGAACTGCAGTTACAAAACTAGTATAAAC
AATTTACAGTGGTATAGACAAAATTCAGGTAGAGGCCTTGTCCACCTAAT
TTTAATACGTTCAAATGAAAGAGAGAAACACAGTGGAAGATTAAGAGTCA
CGCTTGACACTTCCAAGAAAAGCAGTTCCTTGTTGATCACGGCTTCCCGGG
CAGCAGACACTGCTTCTTACTTCTGTGCTACGCTTTACAATGCCAGACTCA
TGTTTGGAGATGGAACTCAGCTGGTGGTGAAGCCAAATATCCAGAACCCT
GAC

FIG. 5C
Clone a-TCRβ-BV6-2BJ1-1 (SEQ ID NO: 21)

ATGAGCCTCGGGCTCCTGTGCTGTGGGGTCTTTTCTCTCCTGTGGGCAGGT
CCAGTGAATGCTGGTGTCACTCAGACCCCAAAATTCCGGGTCCTGAAGAC
AGGACAGAGCATGACACTGCTGTGTGCCCAGGATATGAACCATGAATACA
TGTACTGGTATCGACAAGACCCAGGCATGGGCTGAGGCTGATTCATTAC
TCAGTTGGTGAGGGTACAACTGCCAAAGGAGAGGTCCTGATGGCTACAA
TGTCTCCAGATTAAAAAAACAGAATTTCCTGCTGGGGTTGGAGTCGGCTG
CTCCCTCCCAAACATCTGTGTACTTCTGTGCCAGCAGGTCCGGGTCGGCGG
GAGCTTTCTTTGGACAAGGCACCAGACTCACAGTTGTAGAG

Fig. 5D
Clone b-TCRα-AV27AJ20 (SEQ ID NO: 22)

ATGGTCCTGAAATTCTCCGTGTCCATTCTTTGGATTCAGTTGGCATGGGTG
AGCACCCAGCTGCTGGAGCAGAGCCCTCAGTTTCTAAGCATCCAAGAGGG
AGAAAATCTCACTGTGTACTGCAACTCCTCAAGTGTTTTTTCCAGCTTACA
ATGGTACAGACAGGAGCCTGGGGAAGGTCCTGTCCTCCTGGTGACAGTAG
TTACGGGTGGAGAAGTGAAGAAGCTGAAGAGACTAACCTTTCAGTTTGGT
GATGCAAGAAAGGACAGTTCTCTCCACATCACTGCGGCCCAGCCTGGTGA
TACAGGCCTCTACCTCTGTGCAGGGAAGAAGACTAACGACTACAAGCTCA
GCTTTGGAGCCGGAACCACAGTAACTGTAAGAGCAAATATCCAGAACCCT
GAC

Fig. 5E
Clone b-TCRβ-BV4-3BJ2-7 (SEQ ID NO: 23)

ATGGGCTGCAGGCTGCTCTGCTGTGCGGTTCTCTGTCTCCTGGGAGCGGTC
CCCATGGAAACGGGAGTTACGCAGACACCAAGACACCTGGTCATGGGAAT
GACAAATAAGGAGTCTTTGAAATGTGAACAACATCTGGGTCATAACGCTA
TGTATTGGTACAAGCAAAGTGCTAAGAAGCCACTGGAGCTCATGTTTGTC
TACAGTCTTGAAGAACGGGTTGAAAACAACAGTGTGCCAAGTCGCTTCTC
ACCTGAATGCCCCAACAGCTCTCACTTATTCCTTCACCTACACACCCTGCA
GCCAGAAGACTCGGCCCTGTATCTCTGCGCCAGCAGCCAGGACAGGGTAA
ACTTGGCGGGAGAGCAGTACTTCGGGCCGGGCACCAGGCTCACGGTCACA
GA

Fig. 9A
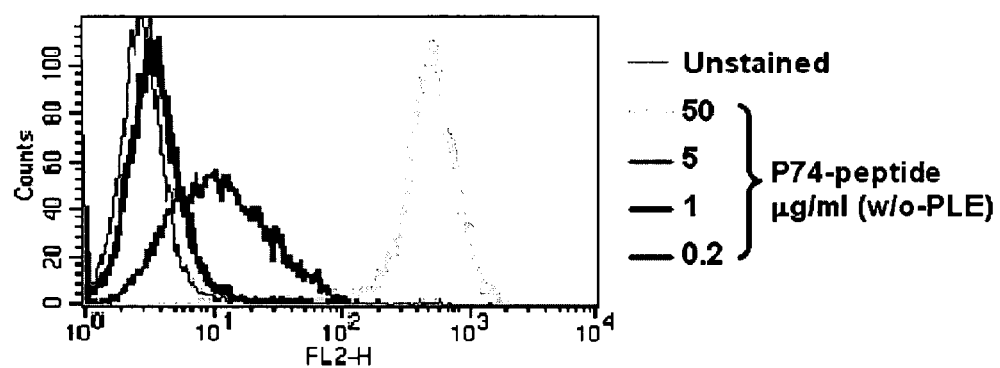
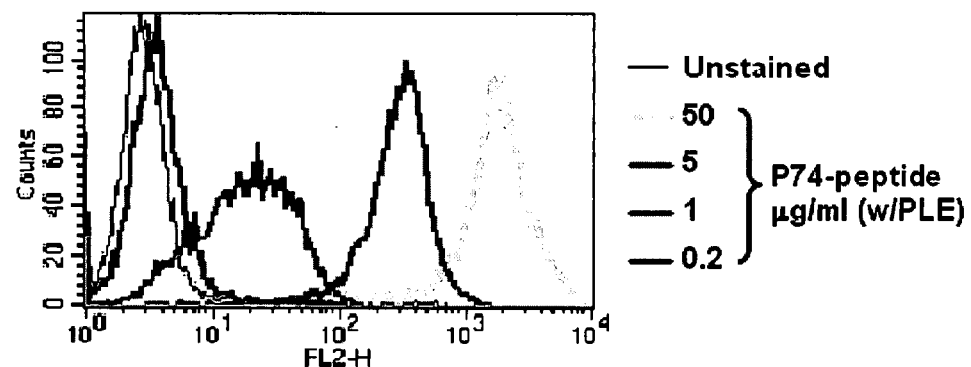
Fig. 9B

Fig. 10A
Fig. 10B
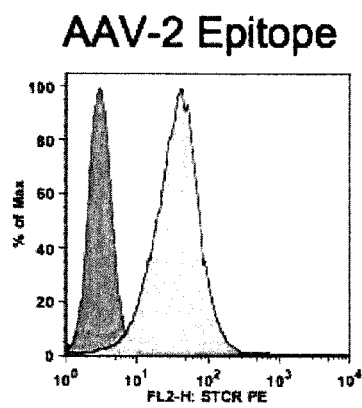
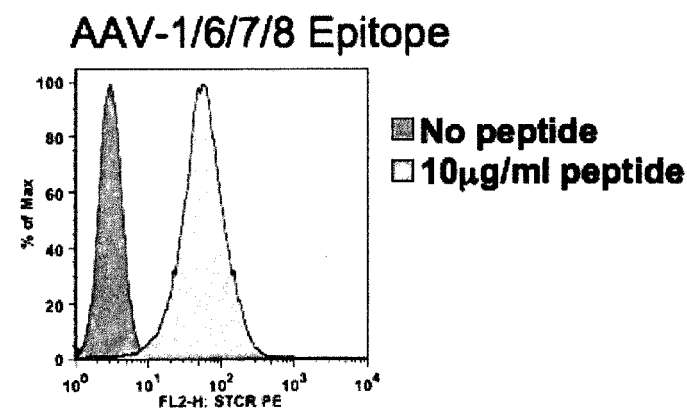

Fig. 11A
Fig. 11B
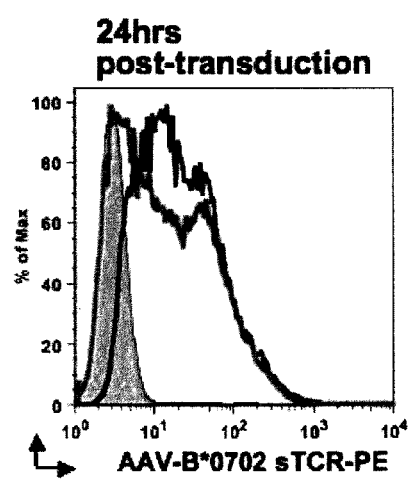
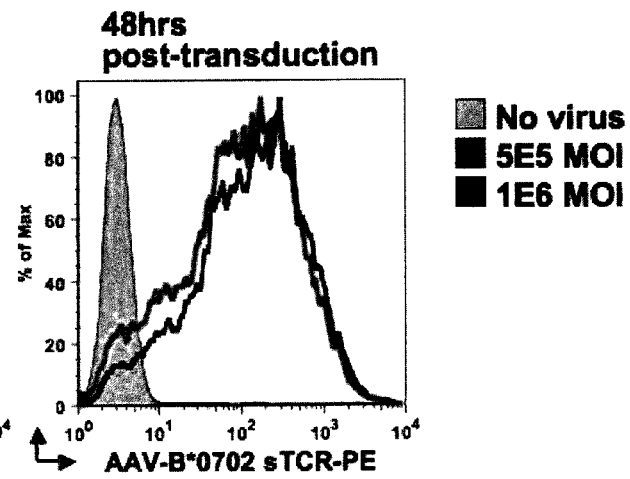

Fig. 12A
Fig. 12B
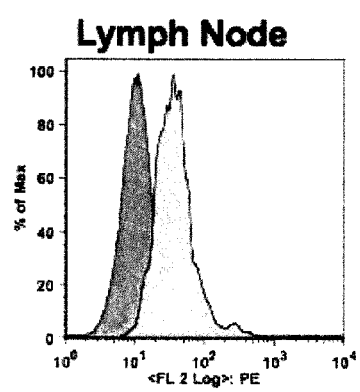
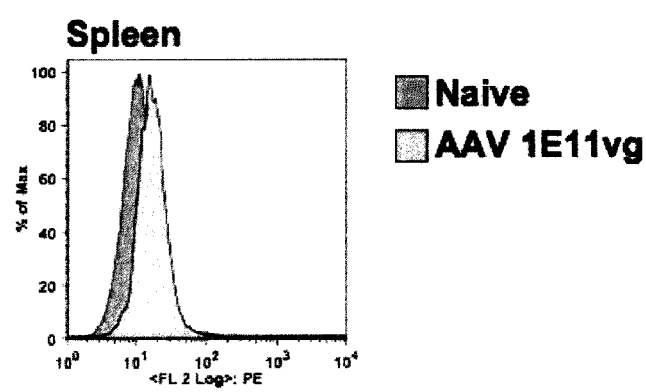

COMPOSITIONS AND METHODS FOR DETECTION AND MODULATION OF T CELL MEDIATED IMMUNE RESPONSES AGAINST VIRAL VECTORS UTILIZED FOR GENE THERAPY

The present application is §371 application of PCT/US2007/070147 filed 31 May 2007 which claims priority to U.S. Provisional Application No. 60/809,956 filed 31 May 2006, the entire disclosures of each being incorporated herein by reference.

Pursuant to 35 U.S.C. §202(c) it is acknowledged that the U.S. Government has certain rights in the invention described, which was made in part with funds from the National Institutes of Health, Grant Number PO1 HL078810.

FIELD OF THE INVENTION

This invention relates to the fields of gene therapy, and immunology. More specifically, the invention provides compositions and methods for detecting the presence of viral vector antigens, including compositions and methods for inhibiting or avoiding the immune response to the same.

BACKGROUND OF THE INVENTION

Several publications and patent documents are cited throughout the specification in order to describe the state of the art to which this invention pertains. Each of these citations is incorporated herein by reference as though set forth in full.

Wild-type AAV is a parvovirus with a ~4.7 kb single-stranded DNA genome. The virus is naturally replication-defective and requires a helper virus such as adenovirus or herpesvirus for replication. The virus has not been associated with any disease but instead was initially isolated as a contaminant of adenoviral isolates (4). Six serotypes have been described, with highly conserved sequences (varying from 62-99%). The viral genome is flanked by two inverted terminal repeats (ITRs), and encodes three capsid genes (VP1, 2, 3) and 4 rep proteins involved in DNA replication and in control of the AAV life cycle. Three additional serotypes (AAV-7, -8, -9) have recently been isolated from Rhesus macaques and humans and are also >60% conserved compared to AAV-1-6 (5).

Wild-type AAV has been engineered for use as a gene delivery vehicle. The rep and cap genes are deleted, and the therapeutic gene of interest inserted between the two ITRs, such that there is no coding viral DNA. In the mid-1990's several groups (6-10) showed that recombinant AAV could infect multiple non-dividing cell types, including skeletal muscle, liver, CNS, and respiratory tract, and could direct long-term expression of a transgene in an immunologically competent animal. This exciting finding has been exploited by a number of groups and there is now an impressive portfolio of results in which genetic diseases have been cured in small and large animal models by the administration of recombinant AAV (11-17). Experience in humans is more limited (18-24), but has been promising in terms of safety and of evidence for gene transfer and expression, although levels of expression have not yet been high enough to produce phenotypic correction in most instances.

One major objective of our research is the establishment of a safe and effective adeno-associated virus (AAV)-mediated gene transfer system for treating hemophilia and other blood coagulation disorders. Based on long-term cure of hemophilia in the canine model of the disease (1), a clinical study was designed in which subjects with severe hemophilia B were infused via the hepatic artery with AAV-F.IX. One subject achieved circulating Factor IX levels of 11.8% (therapeutic range) by the second week after vector infusion. These levels were sustained for approximately four weeks and then gradually began to fall, eventually returning to the subject's baseline level of <1%. Coincident with the fall in F.IX levels, the liver transaminase enzymes in the blood began to rise, peaking at 5 weeks after infusion, and declining to normal several weeks thereafter. Thus, the subject pursued a course quite different from that seen in experimental animals, including mice, rats, rabbits, hemophilic dogs, and non-human primates. In contrast to experimental animals, the human subject had pre-existing immunity to AAV-2, as evidenced by the presence of a low neutralizing antibody titer to AAV; and by inference from the presence of IgG antibodies, the subject also likely had a population of AAV-specific memory T cells in his lymphoid compartment (2). Similar findings were observed in another subject in the trial, and immunologic studies in this subject documented a T cell response to a specific peptide in the AAV capsid. Notably, the response was detectable in the peripheral blood for several weeks after, but not before vector infusion.

In light of these findings, it is clear that in order for gene therapy approaches to be effective, in certain instances, it may be necessary to modulate the immune response to prevent T-cell mediated destruction of transgene expressing cells.

SUMMARY OF THE INVENTION

In accordance with the present invention, soluble T cell receptors (sTCR) which are immunospecific for a peptide sequence present in an adenovirus-associated virus (AAV) in the context of a human MHC Class 1 molecule are disclosed. In a preferred embodiment, the adenovirus peptide sequence is obtained from a serotype selected from the group consisting of AAV-1, AAV-2, AAV-5, AAV-8 and other naturally occurring serotypes. In a particularly preferred embodiment, the peptide has a sequence provided in Table 1 and the human MHC Class 1 molecule is selected from the group consisting of HLA-A1, HLA-A2, HLA-A3, HLA-B7, HLA-B8, HLA-B15, HLA-B44 and HLA-B51.

Also encompassed by the present invention is a method for detecting the presence a T cell mediated immune response against viral capsid antigen before, during or after administration of an adeno-associated viral vector containing a transgene. An exemplary method entails obtaining a biological sample from a patient which comprises T cells; contacting the cells with a pentamer or tetramer comprising a peptide epitope of said capsid in context with an MHC Class 1 molecule; and determining whether said contact stimulates the T cells relative to an untreated control cell, cells being stimulated by said contact having specificity for said peptide epitope of said viral capsid, this specificity being correlated with T cell mediated destruction of capsid and transgene containing cells. The method can also comprise isolating mRNA from said stimulated T cells, preparing cDNA and cloning a soluble T cell receptor immunospecific for said viral capsid antigen.

Soluble T cell receptors prepared by the foregoing method are also encompassed by the present invention.

In yet another aspect, a method for inhibiting T cell mediated destruction of virally transduced cells, after administration of an adeno-virus associated vector is disclosed. An exemplary method entails providing an effective amount of a sTCR having specificity for an AAV epitope/MHC complex, said sTCR preventing T cell mediated destruction of said transgene containing cells via blockage of binding of naturally occurring T cells to the offending capsid peptide. Blockage of such binding will prevent CTL activation.

Additionally, a method for avoiding T cell mediated destruction of virally transduced cells is provided comprising detecting specificity for an AAV peptide epitope as described above and altering the AAV vector to eliminate the peptide epitope identified. Following alteration, the modified AAV vector is then administered to said patient, the alteration abrogating T cell mediated destruction of the virally transduced cells. Such altered AAV vectors also comprise a further aspect of the invention. In a preferred embodiment, such AAV vectors have been modified such that they lack an AAV epitope provided in Table 1.

BRIEF DESCRIPTION OF THE DRAWINGS

FIG. 1 depicts a graph showing the time course of T cell responses in PBMCs isolated from a patient treated with an AAV vector containing a transgene.

FIG. 2A is a graph showing the results of AAV Capsid IFN-γ ELISpot. Human lymphocytes restimulated in vitro with AAV-derived peptides produce IFN-γ. FIG. 2B shows a series of scatter plots showing that AAV-specific CD8+ T cells can be expanded in vitro from normal donor peripheral blood mononuclear cells (PBMCs) through several rounds of in vitro stimulation (IVS) with AAV capside-derived immunodominant epitopes.

FIG. 3 shows the different T cell epitopes identified by ELISPOT assays (underlined) which are highly conserved in AAV serotypes 1-8. Shown are SEQ ID NOS: 1-18.

FIGS. 4A and 4B are a pair of scatter plots of two CD8+ T cell clones selected by flow sorting and subsequently expanded in vitro. These clones represent the source of mRNA used to synthesize the soluble T cell receptor described herein.

FIGS. 5A-5E show the sequences of TCRs for CTL clones described hereinbelow.

FIG. 6 is an SDS PAGE of AAV-a-scTCR-BirA and AAV-b-scTCR-BirA. Lane 1, MW standard, Lane-2: AAV-a-scTCR-BirA; Lane 3, AAV-b-scTCR-BirA.

FIG. 7A is a graph showing W4F detection of purified AAV-scTCRs by ELISA. FIG. 7B is graph showing pentamer detection of purified AAV-scTCRs by ELISA.

FIG. 8 is plot showing p74/HLA-B7 binding activity of AAV-scTCR multimer.

FIGS. 9A and 9B shows histograms of p74/HLA-B7 binding of AAV-scTCR multimer.

FIGS. 10A and 10B are a pair of histograms showing in vitro staining of peptide-loaded fibroblasts with aAV-scTCR multimer.

FIGS. 11A and 11B are a pair of histograms showing in vitro staining of AAV-transduced HLA-B*0702 human fibroblasts with AAV-scTCR multimer.

FIGS. 12A and 12B are a pair of histograms showing AAV-scTCR multimer staining of CD11c+CD19− cells collected from HLA B*0702 mice one week after intravenous infusion of 1E11 vector genomes (vg) of AAV.

DETAILED DESCRIPTION OF THE INVENTION

Viral vectors have been engineered for use as gene-transfer vehicles to correct genetic defects. However, in accordance with the present invention, it has been discovered that following administration of transgenes in viral vectors, the corrected liver cells harbor vector capsid proteins. These proteins are detected by T cells which in turn destroy the corrected cells. Thus, one aspect of the invention entails the use of soluble T cell receptors (sTCR) as new reagents to detect the presence of viral vector antigen in tissue that has been targeted for gene transfer. Previous methods for detecting viral vector sequences or capsid proteins have employed PCR or immuno-specific antibodies. However, it appears that a more clinically relevant form is that of vector capsid as it is encountered by host T cells: that is, capsid-derived peptides presented on host MHC Class I. Soluble TCRs are disclosed which detect this form of capsid antigen in a manner comparable to that observed in naturally occurring T cells. These reagents can then be used to directly and quantitatively assess transduced tissue for the presence of vector-derived antigen. This information provides the clinician with the necessary information for determining if and when to withdraw immunosuppressive treatment.

In another aspect of the invention, the soluble TCR reagent could be used as a specific immunomodulatory therapeutic to specifically block the host T cells from encountering their cognate vector antigen. Accordingly, the molecules described herein have utility both as diagnostic and therapeutic agents.

Various serotypes of AAV are in use in the field of gene transfer, and there is great variability of HLA types in the human population. Accordingly, encompassed by the present invention are soluble TCRs designed to be specific for 1) multiple HLA-restricted epitopes and 2) the particular serotype of AAV used in the gene therapy vector.

Alternative AAV Vector Serotypes and Their T Cell-Restricted Epitopes

Despite the sequence similarity of various AAV serotypes, particularly among AAV-1, 2, 5, and 8, there is a possibility that a T cell-directed response to an epitope of one naturally-acquired AAV virus will not cross-react with an alternative serotype used as a gene therapy vector. Because T cell receptors recognize only a small peptide (9-11 amino acids) in an MHC Class I-restricted fashion, and the T cell receptor is exquisitely specific, T cells directed to an AAV-2 epitope, for example, may or may not recognize an epitope from AAV-8 that differs by only one amino acid. Furthermore, the peptide epitopes from any AAV virus will be restricted by an individual's HLA (the human version of MHC) type. Thus, based on the likelihood that several T cell-restricted epitopes of AAV will be conserved among AAV serotypes, we have identified various AAV epitopes from several serotypes that will be restricted to HLA types common in the population, including HLA-A1, A2, A3, B7, B8, B15, B44, and B51. In fact, in functional assays, we have developed a library of several candidate epitopes from AAV-1, AAV-2, and AAV-8 (Table 1). The application of soluble TCRs to detect vector capsid sequences could thus be easily expanded from the single HLA-B7-restricted AAV epitope we already have (AAV-2 VPQYGYLTL) to multiple epitopes from any of the AAV serotypes currently in use as putative gene therapy vectors.

In addition to the production of MHC class I pentamers and soluble TCRs, the identification of immunodominant epitopes can be useful to engineer AAV capsid proteins, eliminating the offending epitopes. Once the epitopes are known, the corresponding sequence within the AAV capsid sequence can be eliminated using standard molecular biology/recombinant DNA techniques. Thus, another aspect of the invention entails re-engineering of the capsid to alter the identified T cell epitope. This will result in a vector that avoids the previously described specific T cell response. Note that this would give rise to a series of vectors, each specific to a given MHC haplotype, that would avoid the T cell responses seen in previous clinical studies (3). Note that this invention would apply for all AAV serotypes, as indicated by the data in Table 1

TABLE 1

| HLA allele | AAV-1 Epitopes | AAV-2 Epitopes | AAV-8 Epitopes |
|---|---|---|---|
| HLA A*01 | AGDNPYLRY (24) | SGDNPYLKY (27) | AGDNPYLRY (30) |
| | KTDNNNSNF (25) | SADNNNSEY (28) | TNDNTYFGY (31) |
| | SNDNHYFGY (26) | QLDSGDNPY (29) | RSSFYCLEY (32) |
| HLA A*02 | LIDQYLYYL (33) | LIDQYLYYL (36) | LIDQYLYYL (39) |
| | CLPPFPADV (34) | CLPPFPADV (37) | CLPPFPADV (40) |
| | TLNNGSQAV (35) | TLNNGSQAV (38) | TLNNGSQAV (41) |
| HLA A*03 | *PLMGGFGLK* (42) | *PLMGGFGLK* (45) | PLMGGFGLK (48) |
| | *VLEPLGLVE* (43) | *VLEPLGLVE* (46) | GIREWWALK (49) |
| | QLKAGDNPY (44) | PVKTAPGKK (47) | EVTQNEGTK (50) |
| HLA B*07 | *IPQYGYLTL* (51) | VPQYGYLTL (54) | IPQYGYLTL (57) |
| | FPMSGVMIF (52) | APSGLGTNT (55) | APSGVGPNT (58) |
| | QPAKKRLNF (53) | VPANPSTTF (56) | KPGAPKPKA (59) |
| HLA B*08 | TTSTRTWAL (60) | TTSTRTWAL (63) | TTSTRTWAL (66) |
| | RPKRLNFKL (61) | RPKRLNFKL (64) | RPKRLSFKL (67) |
| | *QAKKRVLEP* (62) | QAKKRVLEP (65) | APKPKANQQ (68) |
| HLA B*15 | *PLIDQYLYY* (69) | *PLIDQYLYY* (71) | PLIDQYLYY (73) |
| | QLKAGDNPY (70) | YHLNGRDSL (72) | KLNSFITQY (74) |
| HLA B*44 | PEVQYTSNY (75) | PEIQYTSNY (77) | PEIQYTSNY (79) |
| | SEYQLPYVL (76) | SEYQLPYVL (78) | SEYQLPYVL (80) |
| HLA B*51 | *IPQYGYLTL* (81) | VPQYGYLTL (84) | *IPQYGYLTL* (87) |
| | VATERFGTV (82) | VPANPSTTF (85) | IANNLTSTI (88) |
| | FPMSGVMIF (83) | FPQSGVLIF (86) | TAPGKKRPV (89) |

Bold: 100% conserved epitopes; SEQ ID NOS in parentheses
In certain embodiments, use of the VPQYGYLTL from AAV-2 epitope is excluded.

Applications of the Soluble TCR Technology

The sTCRs can be employed as immunomodulatory drugs. For example, the soluble TCR can be used to block epitope-MHC class I complex recognition by T cells, therefore preventing harmful T cells responses following AAV vector infusion for gene transfer purposes. For this purpose, the soluble TCR will be administered right before or at the time of AAV vector infusion.

sTCRs may also be used reagents for staining of AAV capsid epitopes on the surface of AAV-injected tissues. One of the most important questions for the field of gene therapy is how long the peptides derived from the degradation of AAV capsid inside the cells are presented on the membrane surface in complex to the MHC molecules, and therefore detectable by the immune system. The soluble TCR reagent described herein can be used to advantage to stain tissue biopsies for AAV epitope-MHC complexes, helping determining the duration of AAV capsid antigen presentation. The determination of the window of time during which subjects undergoing gene therapy are at risk of mounting harmful immune responses to the AAV capsid is essential for the design of effective immunosuppression regimens.

The definitions set forth below are provided to facilitate an understanding of the present invention.

As used herein the phrase "soluble T cell receptor or sTCR" refers to soluble T-cell antigen receptor (monomer or multimer) that can be used to evaluate peptide antigen presentation in the context of MHC molecules on virally infected cells. The soluble TCR can optionally be conjugated with different indicator molecules for use in flow cytometry and immunohystochemistry. Methods for making soluble T cell receptors are disclosed in U.S. Pat. No. 6,080,840, WO/2005/116646 and in Boulter et al. (2003) Protein Engineering 16:707-711.

A "pentamer" is a complex of 5 MHC class I molecules bound to a peptide epitope. All 5 complexes are held in a planar configuration and available for binding to T cell receptors. Pentamers are optionally conjugated to fluorochromes that allow the detection of the cognate antigen-specific T cells by flow cytometry. Note that tetramer technology is also available wherein a complex of 4 MHC Class I molecules are bound to a peptide epitope.

"Pentamer or tetramer staining" refers to a process wherein T cells are mixed with a pentamer or tetramer, incubated at 4° C. for 30 minutes, washed with PBS 1% FBS, and detected by flow cytometry. Reagents suitable for performing such staining assays are commercially available from ProImmune.

The phrase "cytotoxic T cell response" refers to a T cell mediated process of destruction wherein effector CD8+ T cells kill target cells that present epitopes bound to MHC class I molecules on their external surfaces.

The following example is provided to illustrate certain embodiments of the invention. It is not intended to limit the invention in any way.

Example I

As mentioned previously, in a prior gene therapy trial for the treatment of hemophilia, we noted that while expression of the transgene was initially high, over time liver enzymes became slightly elevated and transgene expression was lost. Using peripheral blood mononuclear cells (PBMC) from a subject before and after vector infusion, we were able to define an MHC Class I-restricted epitope in the AAV capsid (3) and synthesize soluble forms of pentameric HLA-B*0702/AAV peptide (pentamers) to detect AAV-specific CD8+ T cells. Using these pentamers, we were able to detect specific T cell expansion in the peripheral blood of this subject to the specific AAV epitope in a time course coincident with the rise in liver transaminases and the decline in transgene expression. See FIG. 1. The observed T cell expansion was observed only in the presence of MHC/peptide antigen. Thus, the evidence presented herein reveals that cytotoxic T cells respond to vector capsid protein presented by transduced hepatocytes. Given that vector capsid protein is present for a limited time after vector infusion, the methods disclosed herein include a 4-month course of immunosuppression in patients in need thereof to temporarily halt T cell function around the time of vector infusion.

Priming of the T cell response is thought to require antigen presentation by professional antigen presenting cells (APCs) such as dendritic cells. Professional APCs are present in the periphery, where they can encounter viral antigens either by direct infection or by phagocytosis of virally-infected cells (cross-presentation). Dendritic cells will then process the antigens, travel to the regional lymph nodes, and present the antigens to naïve T cells in the context of MHC Class I and II and appropriate co-stimulation. After an initial proliferative burst, the frequency of AAV-specific $CD8^+$ T cells would be expected to decline, leaving behind a small pool of memory T cells, which through homeostatic proliferation are maintained throughout the life of an individual (2). Once the adaptive immune system has been primed, the requirements for co-stimulation and antigen presentation by professional APCs become less stringent; memory T cells can recognize and kill cells presenting viral antigens in the context of only MHC Class I, which all nucleated cells possess. Although AAV-2 on its own fails to induce inflammatory reactions needed for priming a T cell response, because natural infection occurs in combination with a helper virus, $CD8^+$ T cells directed to the antigens of both the helper virus and of AAV are primed at that time.

Figure 2A:
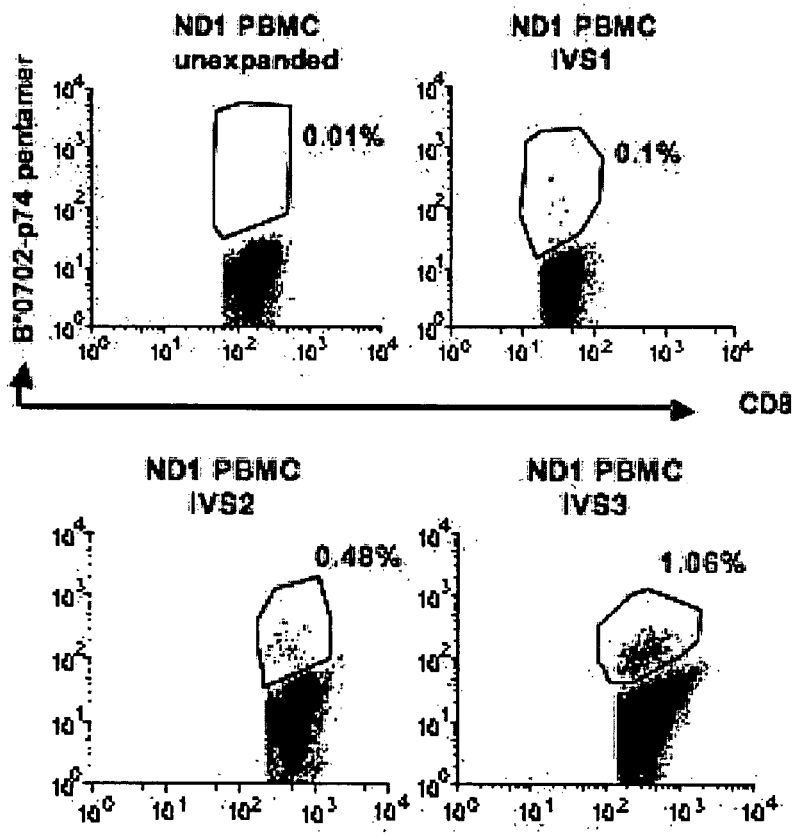
Figure 2B:
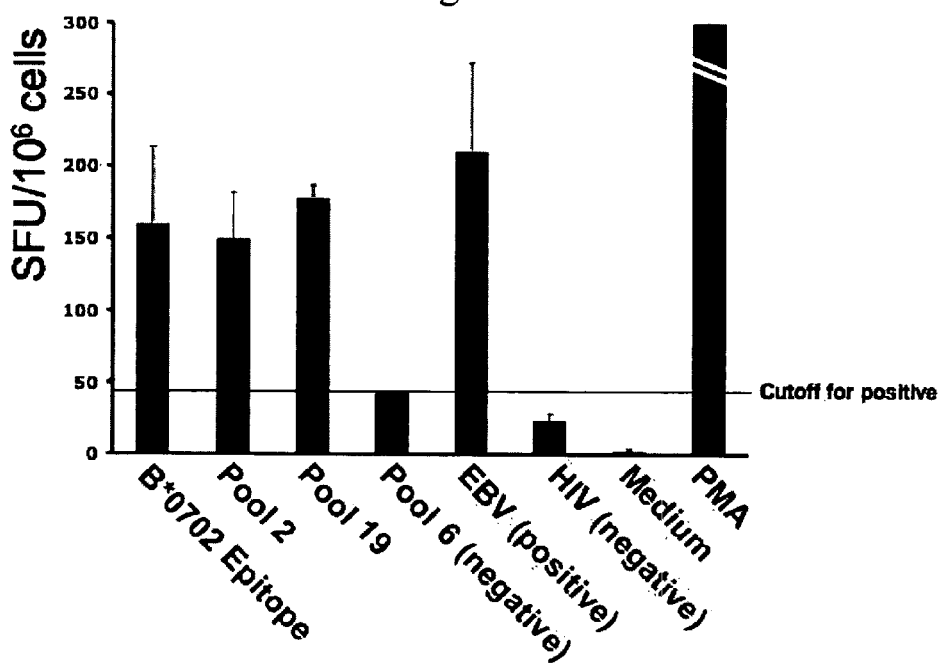

The inflammatory response that is required to prime T cells is not required to recruit and activate memory T cells that re-encounter antigen. Unlike experimental animals, humans are naturally infected by AAV-2 during childhood. There have been very few reports of analysis of T cell responses to AAV in the general population. Chirmule et al. reported that 5% of normal controls showed a stimulation index of >2 after incubation of PBMCs with recombinant AAV (25). Since then, more sensitive and quantitative assays for T cell analysis have been developed, allowing us to pursue a detailed characterization of anti-viral T cell responses in human subjects. We have been able to document T cell responses to AAV in several normal adult donors, indicating that memory T cell responses to viral capsid will be a widespread problem in gene transfer studies using AAV vectors. Human lymphocytes can be expanded in vitro with peptide epitopes derived from the AAV capsid protein sequence. Expanded cells respond to epitopes by producing IFN-γ (FIG. 2A) and can be stained with AAV-specific MHC class I pentamers (FIG. 2B). FIG. 3 depicts a series of different T cell epitopes (see underlining) identified by ELISPOT assays which are highly conserved in AAV serotypes 1-8.

Because there is no viral DNA in gene therapy vectors, the only viral antigen that can be presented to T cells by MHC Class I is the vector capsid protein that is infused, which should be present for a limited amount of time. However, there is currently no direct way to determine the length of time that the capsid is present in such an immunologically detectable form. Although we have chosen a 4-month course of immunosuppression in the continuation of our clinical study, this timeframe is not based on hard evidence of the kinetics of capsid degradation; one reason to determine the length of time that capsid is present is to determine when to withdraw immunosuppression and yet retain the gene-corrected cells.

Several studies have been conducted to determine how long vector capsid is present with different, indirect methods. In our clinical study, we used PCR in a biodistribution study to detect the presence of vector genomes over time. However, PCR detects vector DNA, which is not the form recognized by the problematic T cells. Similarly, antibodies to vector capsid will not detect the vector in the form that is recognized by T cells, which only recognize antigen in the form of an MHC+ peptide complex. Our laboratory is also conducting studies in animal models to address the same question; however, we will ultimately need to determine the persistence of capsid in human subjects, within the specific tissues that are targeted for gene transfer, and for any of the different serotypes of AAV that we may use (though our laboratory in only focused on AAV-2, other gene therapy labs are focused on AAV-1, AAV-5, and/or AAV-8 or chimeras of these). Thus, a functional assay based on T cell responses to vector-transduced tissues is disclosed herein, but ideally these data will be interpreted in conjunction with data using the soluble TCRs also described. These sTCRs would allow direct, quantitative determination of capsid presence, even in the individual human patient that has been treated with vector if a tissue biopsy sample is available.

As shown above, human lymphocytes can be expanded in vitro with peptide epitopes derived from the AAV capsid protein sequence. Expanded cells respond to epitopes by producing IFN-γ and can be stained with AAV-specific MHC class I pentamers (FIGS. 2A and 2B).

Figure 4A:
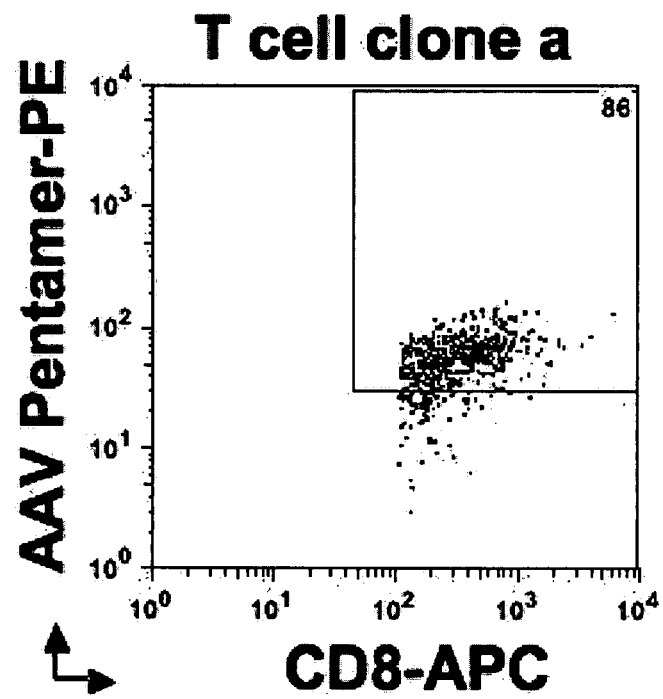
Figure 4B:
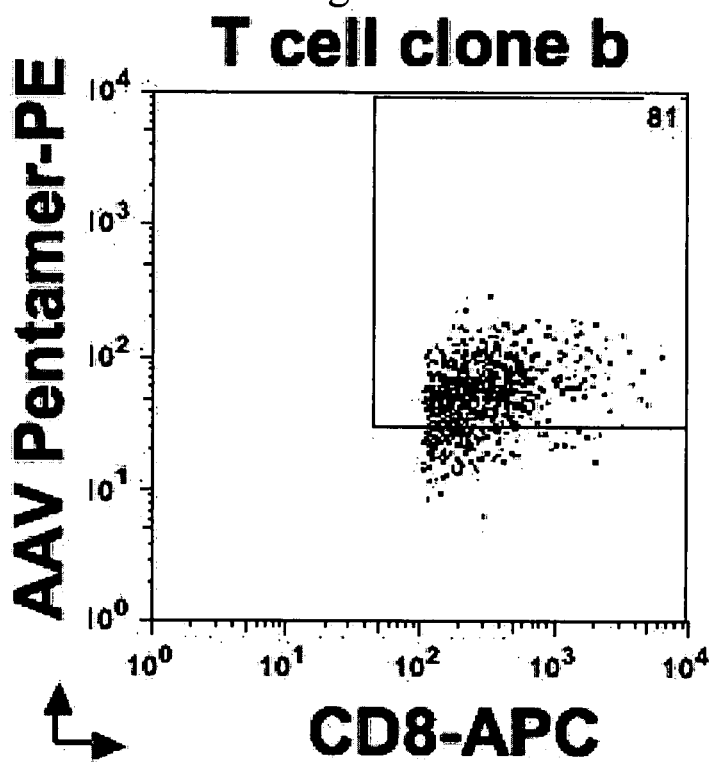

Using an AAV-specific MHC class I pentamer, it is possible to perform flow sorting on expanded capsid-specific CD8+ T cells and select clones of CD8+ T cells (FIGS. 4A and 4B).

Two different human AAV-p74 peptide-specific CTL clones were used to generate T cell receptor (TCR) α and β chain cDNA by a SMART-RACE method employing TCR specific primers. The cDNA products were cloned and sequenced. Two TCR α a chain genes (AV17/TRAJ43; SEQ ID NO: 19) and AV17/AJ31; SEQ ID NO: 20) and one TCR β chain gene (BV6-2/BJ1-1; (SEQ ID NO: 21)) were cloned from CTL clone a. One TCR α chain gene (AV27/AJ20; SEQ ID NO: 22) and one TCR β chain gene (BV4-3/BJ2-7; SEQ ID NO: 23) were cloned from CTL clone b. The sequences of TCRs for two CTL clones are provided in FIGS. 5A-5E.

Figure 6:
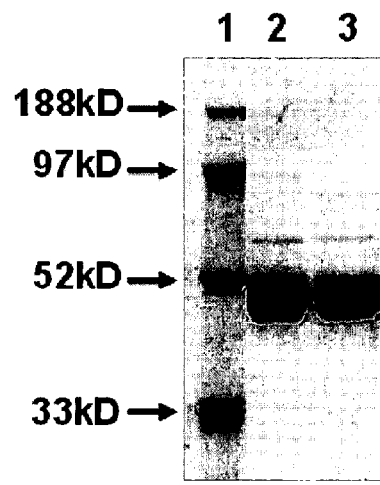
Figure 7A:
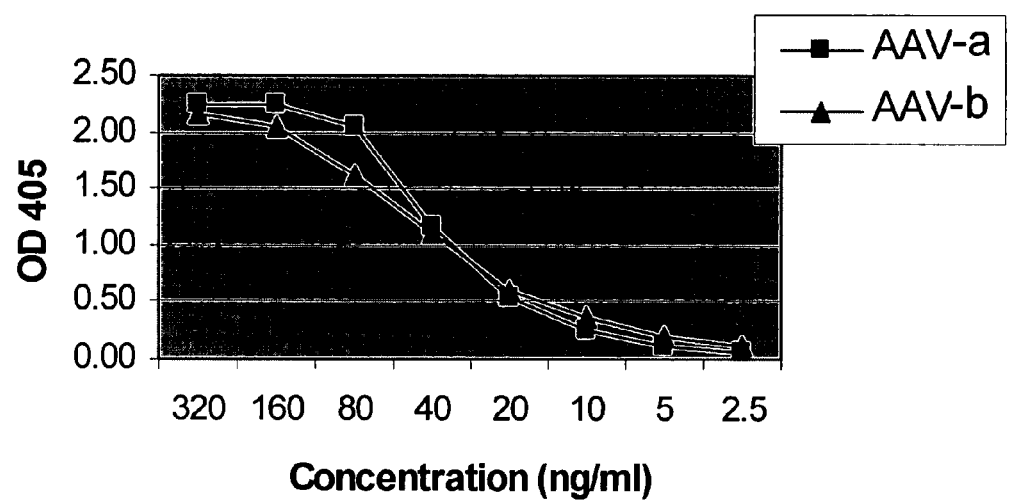

One scTCR fused to the bacterial biotin ligase (scTCR-BirA construct was generated for clone b and two different scTCR-BirA constructs for clone a based on the two α-chains identified. Three expression vectors were produced and transfected into CHO cells to generate soluble scTCR-BirA fusion proteins for characterization. All of three scTCRs can be expressed in AAV-scTCR transfected CHO cells as detected in cell culture supernatants by sandwich ELISA using anti-human TCR β-chain antibodies, (BF1-) 8A3.31 and W4F.5B, available from ATCC. Cell culture supernatants containing clone b scTCR and clone a scTCRs (AV17/AJ31:BV6-2/BJ1-1) showed AAV p74-pentamer binding activity detected by ELISA, and were characterized further. AAV-scTCR-BirA fusion proteins were purified from the culture supernatants of AAV-scTCR-BirA transfectants with BF1-affinity chromatography. The purified fusion proteins are shown in SDS-PAGE (FIG. 6). The fusion protein yields of AAV-a and AAV-b culture supernatants are 4 mg/L and 0.2 mg/L respectively. Characterization of purified scTCR-BirA fusion proteins was done by ELISA. See FIGS. 7A and 7B. To determine whether the purified AAV-p74-scTCR-BirA fusion proteins were recognized by anti-TCR antibodies, serial dilutions of the fusion proteins were incubated with anti-TCR BF1 mAb-coated plate, then detected with biotinylated—anti TCR W4F mAb and SA-HRP. The results are shown in FIG. 7A. To test functional binding affinity of soluble AAV-p74-scTCRs, serial dilutions of the fusion proteins were incubated with anti-TCR BF1 mAb-coated plate, then detected with biotinylated—AAV-p74/HLA-B*0702 pentamer and SA-HRP. See FIG. 7B.

Figure 8:
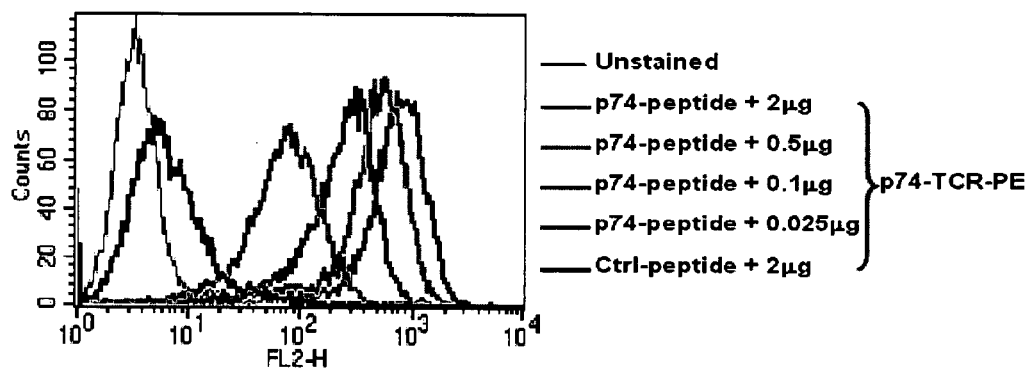

Since the purified AAV-b fusion protein demonstrated much lower pentamer binding activity than AAV-a-AJ31 only AAV-a-AJ31 fusion protein was biotinylated and used to generate soluble p74-scTCR-PE multimer. AAV-p74 peptide loaded HLA-B7-positive human lymphoblastoid cell line (JyA2B7) was used to determine whether AAV-a-scTCR can bind to AAV-p74 peptide/HLA-B7 complexes on cell surface. Specific staining of JyA2B7 (immortalized B cells) cells loaded with 50 µg/ml of AAV-p74 peptide was observed with 0.025 µg/test of PE-conjugated p74-scTCR multimer (FIG. 8).

Figure 7B:
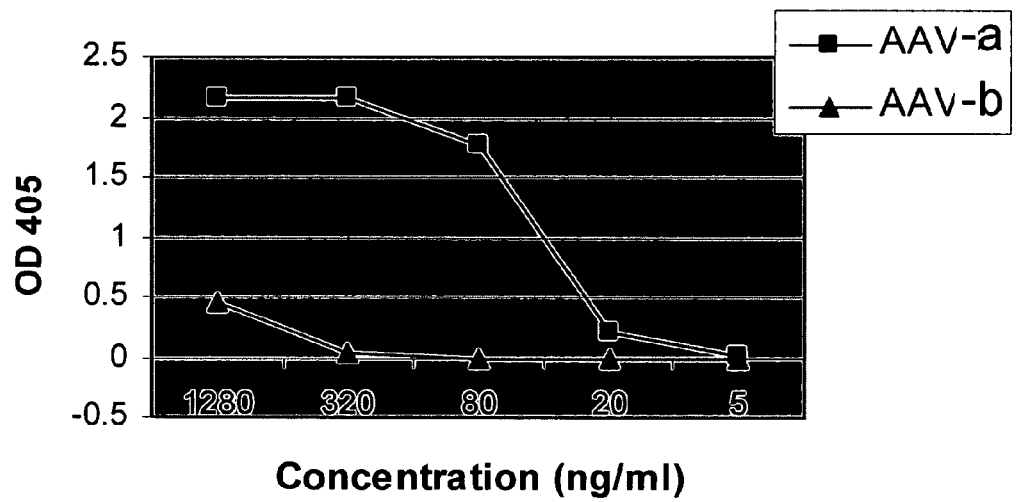

On the other hand 0.5 µg of p74-scTCR multimer can stain JyA2B7 cells loaded with a minimum of 5 µg/ml AAV-p74 peptide under typical conditions (FIG. 9A) or a minimum of 1 µg/ml AAV-p74 peptide when PLE was added during loading (FIG. 7B). (PLE is a proprietary mixture of reagents from Altor BioScience Corp., Miramar, Fla. that enhances peptide loading on antigen presenting cells).

AAV-scTCR multimer was tested in vitro using a normal human fibroblast cell line positive for HLA-B*0702 (Malme-3 available from the ATCC repository). Cells were peptide loaded with AAV capsid epitopes at a concentration of 10 µg/ml for 2 hrs at 37° C. and then stained with the AAV-scTCR multimer (FIG. 10); alternatively, cells were transduced with an AAV vector at an MOI of $5 \times 10^5$ or $1 \times 10^6$ and stained 24 or 48 hours later (FIG. 11). In both experiments a positive staining for the AAV-scTCR multimer was observed indicating that the multimer binds with good affinity to MHC molecules displaying the AAV peptide epitopes.

Similarly, lymph node cells and splenocytes collected from HLA-B*0702 transgenic mice after the administration of an AAV vector intravenously show positive staining for the AAV-scTCR multimer (FIG. 12).

CONCLUSION

An exemplary soluble TCR that is specific for the AAV2 peptide (sequence VPQYGYLTL) in the context of the human MHC Class I molecule HLA-B*0702 is described herein. We have expanded T cells specific for this peptide from an anonymous normal donor with HLA-B*0702 haplotype. T cells specific for this peptide have been cloned and DNA for their T cell receptors isolated and expressed.

There are several groups who have developed soluble TCRs in order to study and quantitate levels of viral and/or tumor antigen expression (26-31). Engineering soluble TCRs has been difficult for a variety of reasons, including the low affinity of naturally occurring T cell receptors for MHC/peptide, and the low expression of specific peptide/MHC complexes on a particular cell. In the published studies of TCRs, the affinity of TCRs to peptide/MHC complexes has been assessed (30). Examination of levels of MHC/peptide antigen have focused on mouse allo-antigen (28) and HTLV-1 antigen as a causal antigen in neurologic disorders (infection (28) and paraneoplastic disease (27)). One study has also used soluble TCRs to better understand the development of the T cell repertoire (26), and another group has also used soluble TCRs to target viral entry (29). Finally, Zhu et al (2006) have constructed a multimeric single-chain soluble TCR to visualize tumor-antigen-derived peptides presented on human MHC Class I in tumor cells. There are no published studies to our knowledge examining the presence of viral vector-derived antigens, either in human, animal, or in vitro models; there are also no published studies on AAV-derived antigens, except for our recent paper describing the HLA B*0702 restricted epitope we have found (3).

The methods set forth below are provided to facilitate the practice of the present invention.

Identification of AAV Capsid Epitopes

Adeno-associated viruses (AAV) belong to the parvoviridae family and naturally infect humans, usually early in life. In order to identify new CD8 T cell epitopes for the most common HLA in the population, two IRB-approved protocols were initiated for the collection of human spleens in collaboration with the Children's Hospital of Philadelphia and the Cooperative Human Tissue Network at the Hospital of the University of Pennsylvania. Spleen offers two main advantages over other tissues for epitope discovery studies; first, it is a lymphoid organ involved in T cell memory maintenance; second, from only one gram of tissue it is possible to isolate up 500 million cells, a number not easily obtainable from other sources like whole blood.

T Cells Isolation and HLA Typing

T cells are isolated within 24 hrs from tissue harvest. Spleens are first processed into small pieces with a scalpel and then homogenized. After red cell lysis, splenocytes are washed twice in PBS and frozen in human serum with 10% DMSO in aliquots of about 10 million cells each.

Two or more aliquots of cells are sent to the HLA typing lab at the University of Pennsylvania Hospital for high-resolution HLA typing.

In Vitro T Cell Expansion

Identification of CD8 T cell epitopes is hindered by the low frequency of memory CD8 T cells reacting to the AAV capsid protein. In order to overcome this limitation, lymphocytes from spleen tissue are expanded in vitro with a series of peptides derived from the AAV capsid protein called VP1. The VP1 peptide library is composed of 145 15-mers derived from the protein sequence, each overlapping by 10 aminoacids (Mimotopes).

Briefly, lymphocytes from spleens are plated in a 96 well plate at one million cells per well in AIM-V (Gibco) medium with 3% heat inactivated human serum, half of the cells in the well are irradiated at 3000 rads and serve as a feeder layer. Each peptide from the VP1 library is added to a single well at a final concentration of 10 µg/ml. At day 0 of expansion and every 2-3 days IL-2 (Roche) is added to cultures at a final concentration of 10 U/ml.

One round of stimulation lasts for 7-10 days, due to the expected low number of CD8 T cells reacting to the AAV capsid, usually two-three rounds of expansion are needed. Each additional round of expansion is simply performed by adding new peptide to the wells and 500,000 autologous spleen cells that have been irradiated at 3000 rads.

Epitope Search by IFN-Gamma ELISpot

ELISpot is a powerful technique used to identify the number T cells reacting to a specific antigen; ELISpot measures the ability of cells of secreting IFN-gamma in response to a peptide. 50,000 expanded T cells were plated in 96 well ELISpot plates (Millipore) previously coated with anti-human IFN-gamma (Mab-Tech) in the presence of the peptide used for expansion. After 24 hrs of incubation at 37° C., 5% $CO_2$, cells are washed off and a secondary anti-human IFN-gamma biotinylated antibody (Mab-Tech) is added to the wells. A streptavidin-alkaline phosphatase is used as detecting reagent in the presence of a specific substrate.

A positive well is judged based on the number of spot forming cells (SFC) per million cells initially added; if the number of SFC is three times higher than the number of SFC in the negative control well (medium only), the well is considered positive. Positive peptides are usually confirmed at least twice by repeating the protocol described above.

This procedure is then repeated for all the HLA alleles of interest.

On-Line Prediction Algorithm

Two on-line epitope prediction programs are used to identify a 9-mer subsequence within the 15-mer peptides used on the ELISpot assay, which represents the binding sequence to the HLA molecule. These programs can be found on the web at Rankpep:http://bio.dfci.harvard.edu/Tools/rankpep.html and SYFPEITHI: www.syfpeithi.de/.

The identified 9-mers are synthesized and confirmed by ELISpot and intracellular cytokine staining. The sequence of the positive peptide epitopes is then used to synthesize HLA-peptide pentamer reagents (Proimmune).

Use of Pentamers for Sorting and Cloning of AAV-Specific T Cells

Peripheral blood mononuclear cells (PBMC) that have been expanded once or twice with a specific AAV peptide can be stained in a sterile fashion with the appropriate HLA-peptide pentamer. The staining can be carried out in sterile PBS with 2% human serum for 20 minutes at 4° C., as for pentamer staining that is usually only used for analysis. The culture can be co-stained with anti-CD8 antibody. After two washes in PBS-2% hAB serum, the cells can be run through a fluorescence-activated cell sorter and sorted to include one pentamer+CD8+ T cell per well of a 96-well round bottom plate. Cells can be sorted into five to ten plates. Each well of each plate can be prepared on the same day to include irradiated allogeneic PBMC as feeder cells, along with irradiated cells from an EBV-transformed B cell line, and an anti-CD3 T-cell stimulatory antibody that is commercially available (OKT3) in addition to 50 IU/ml recombinant human IL-2 as a T cell growth factor. The sorted (cloned) cells can then be incubated in a humidified 37° C. incubator for two weeks.

After two weeks, the growth of T cell clones will be assessed by visual inspection. Growing cells will be assayed for specificity to AAV by a pentamer stain (as described above). Clones that retain peptide-specificity will be further stimulated with allogeneic PBMC, irradiated EBV-transformed B cells, OKT3, and IL-2 as per the first stimulation, except that the growing cells will be transferred to a 24-well plate or a T25 flask depending on how quickly the population is growing. Clones will be re-stimulated every two weeks as described by Dr. Cassian Yee and colleagues (32).

Once at least one million T cells of a clone have grown, aliquots will be frozen as per standard protocols. An aliquot of a T cell clone will be provided to AltorBioscience Corporation for generation of a soluble TCR. Alternatively, we will isolate RNA from a growing T cell clone and provide RNA to AltorBioscience. At this point, RNA will be used to make cDNA and this material will form the basis for generating a soluble T cell receptor by AltorBioscience, a group with experience in generating these molecules (31).

We have successfully cloned and characterized soluble TCR receptors specific for AAV epitopes that are involved in the generation of a cytotoxic T cell response that will hinder gene transfer in patients. The materials and methods described herein can be used both diagnostically and therapeutically to facilitate the introduction of therapeutic heterologous proteins into patients in need thereof.

REFERENCES

1. Mount J D, Herzog R W, Tillson D M, et al. Sustained phenotypic correction of hemophilia B dogs with a factor IX null mutation by liver-directed gene therapy. Blood. 2002; 99:2670-2676.
2. Appay V, Rowland-Jones S L. Lessons from the study of T-cell differentiation in persistent human virus infection. Semin Immunol. 2004; 16:205-212.
3. Manno C S, Arruda V R, Pierce G F, et al. Successful transduction of liver in hemophilia by AAV-Factor IX and limitations imposed by the host immune response. Nat Med. 2006; 12:342-347.
4. Blacklow N R, Hoggan M D, Sereno M S, et al. A seroepidemiologic study of adenovirus-associated virus infection in infants and children. Am J Epidemiol. 1971; 94.
5. Gao G P, Alvira M R, Wang L, Calcedo R, Johnston J, Wilson J M. Novel adeno-associated viruses from rhesus monkeys as vectors for human gene therapy. Proc Natl Acad Sci USA. 2002; 99:11854-11859.
6. Xiao X, Li J, Samulski R J. Efficient long-term gene transfer into muscle tissue of immunocompetent mice by adeno-associated virus vector. j Virol. 1996; 70:8098-8108.
7. Kessler P D, Podsakoff G M, Chen X, et al. Gene delivery to skeletal muscle results in sustained expression and systemic delivery of a therapeutic protein. Proc Natl Acad Sci USA. 1996; 93:14082-14087.
8. Flotte T R, Afione S A, Conrad C, et al. Stable in vivo expression of the cystic fibrosis transmembrane conductance regulator with an adeno-associated virus vector. Proc Natl Acad Sci USA. 1993; 90:10613-10617.
9. Kaplitt M G, Leone P, Samulski R J, et al. Long-term gene expression and phenotypic correction using adeno-associated virus vectors in the mammalian brain. Nat Genet. 1994; 8:148-154.
10. Flotte T R, Carter B J. Adeno-associated virus vectors for gene therapy. Gene Ther. 1995; 2:357-362.
11. Sanchez-Pemaute R, Harvey-White J, Cunningham J, Bankiewicz K S. Functional effect of adeno-associated virus mediated gene transfer of aromatic L-amino acid decarboxylase into the striatum of 6-OHDA-lesioned rats. Mol Ther. 2001; 4:324-330.
12. Acland G M, Aguirre G D, Ray J, et al. Gene therapy restores vision in a canine model of childhood blindness. Nat Genet. 2001; 28:92-95.
13. Ho T T, Maguire A M, Aguirre G D, et al. Phenotypic rescue after adeno-associated virus-mediated delivery of 4-sulfatase to the retinal pigment epithelium of feline mucopolysaccharidosis VI. J Gene Med. 2002; 4:613-621.
14. Mochizuki H, Hayakawa H, Migita M, et al. An AAV-derived Apaf-1 dominant negative inhibitor prevents MPTP toxicity as antiapoptotic gene therapy for Parkinson's disease. Proc Natl Acad Sci USA. 2001; 98:10918-10923.
15. Yue Y, Li Z, Harper S Q, Davisson R L, Chamberlain J S, Duan D. Microdystrophin gene therapy of cardiomyopathy restores dystrophin-glycoprotein complex and improves sarcolemma integrity in the mdx mouse heart. Circulation. 2003; 108:1626-1632.
16. Friedrich O, Both M, Gillis J M, Chamberlain J S, Fink R H. Mini-dystrophin restores l-type calcium currents in skeletal muscle of transgenic mdx mice. J Physiol. 2003.
17. Watchko J, O'Day T, Wang B, et al. Adeno-associated virus vector-mediated minidystrophin gene therapy improves dystrophic muscle contractile function in mdx mice. Hum Gene Ther. 2002; 13:1451-1460.
18. Flotte T, Carter B, Conrad C, et al. A phase I study of an adeno-associated virus-CFTR gene vector in adult CF patients with mild lung disease. Hum Gene Ther. 1996; 7:1145-1159.
19. Wagner J A, Messner A H, Moran M L, et al. Safety and biological efficacy of an adeno-associated virus vector-cystic fibrosis transmembrane regulator (AAV-CFTR) in the cystic fibrosis maxillary sinus. Laryngoscope. 1999; 102 (2 Pt 1):266-274.
20. Wagner J A, Nepomuceno I B, Messner A H, et al. A phase II, double-blind, randomized, placebo-controlled clinical trial of tgAAVCF using maxillary sinus delivery in patients with cystic fibrosis with antrostomies. Hum Gene Ther. 2002; 13:1349-1359.
21. Wagner J A, Reynolds T, Moran M L, et al. Efficient and persistent gene transfer of AAV-CFTR in maxillary sinus. Lancet. 1998; 351(9117): 1702-1703.

22. Wagner J A, Moran M L, Messner A H, et al. A phase I/II study of tgAAV-CF for the treatment of chronic sinusitis in patients with cystic fibrosis. Hum Gene Ther. 1998; 9:889-909.
23. Kay M A, Manno C S, Ragni M V, et al. Evidence for gene transfer and expression of factor IX in haemophilia B patients treated with an AAV vector. Nat Genet. 2000; 24:257-261.
24. Manno C S, Chew A J, Hutchison S, et al. AAV-mediated factor IX gene transfer to skeletal muscle in patients with severe hemophilia B. Blood. 2003; 101:2963-2972.
25. Chirmule N, Propert K, Magosin S, Qian Y, Qian R, Wilson J. Immune responses to adenovirus and adeno-associated virus in humans. Gene Ther. 1999; 6:1574-1583.
26. Holler P D, Chiewicki L K, Kranz D M. TCRs with high affinity for foreign pMHC show self-reactivity. Nat Immunol. 2003; 4:55-62.
27. Laugel B, Boulter J M, Lissin N, et al. Design of soluble recombinant T cell receptors for antigen targeting and T cell inhibition. J Biol Chem. 2005; 280:1882-1892.
28. O'Herrin S M, Lebowitz M S, Bieler J G, et al. Analysis of the expression of peptide-major histocompatibility complexes using high affinity soluble divalent T cell receptors. J Exp Med. 1997; 186:1333-1345.
29. Peng K W, Holler P D, Orr B A, Kranz D M, Russell S J. Targeting virus entry and membrane fusion through specific peptide/MHC complexes using a high-affinity T-cell receptor. Gene Ther. 2004; 11:1234-1239.
30. Subbramanian R A, Moriya C, Martin K L, et al. Engineered T-cell receptor tetramers bind MHC-peptide complexes with high affinity. Nat Biotechnol. 2004; 22:1429-1434.
31. Zhu X, Belmont H J, Price-Schiavi S, et al. Visualization of p53 (264-272)/HLA-A*0201 complexes naturally presented on tumor cell surface by a multimeric soluble single-chain T cell receptor. J Immunol. 2006; 176:3223-3232.
32. Yee C, Savage P A, Lee P P, Davis M M, Greenberg P D. Isolation of high avidity melanoma-reactive CTL from heterogeneous populations using peptide-MHC tetramers. J Immunol. 1999; 162:2227-34.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. An isolated AAV peptide epitope consisting of a peptide sequence, wherein said peptide sequence is selected from the group consisting of SEQ ID NOs: 24-89.

2. The AAV peptide sequence of claim 1 which is SEQ ID NO: 28.

3. The isolated peptide sequence of claim 1, wherein said group excludes SEQ ID NOs: 54 and 84.

4. A method for detecting the presence a T cell mediated immune response against viral capsid antigen before, during or after administration of an adeno-associated viral vector containing a transgene, comprising:
   a) obtaining a biological sample from a patient, said sample comprising T cells;
   b) contacting said cells with a pentamer comprising a peptide epitope of said capsid in context with an MHC Class I molecule, wherein said peptide epitope is selected from the group of peptides claimed in claim 3; and
   c) determining whether the contact of step b) stimulates said cells relative to an untreated control cell, cells being stimulated by said contact having specificity for said peptide epitope of said viral capsid.

5. The method of claim 4, wherein said biological sample comprises cells selected from the group consisting of transgene containing cells, PBMCs, liver cells, epithelial cells, and muscle cells.

* * * * *

SEQUENCE LISTING

```
<160> NUMBER OF SEQ ID NOS: 89

<210> SEQ ID NO 1
<211> LENGTH: 47
<212> TYPE: PRT
<213> ORGANISM: Artificial Sequence
<220> FEATURE:
<223> OTHER INFORMATION: Synthetic Sequence

<400> SEQUENCE: 1

Thr Val Gln Val Phe Ser Asp Ser Glu Tyr Gln Leu Pro Tyr Val Leu
1               5                   10                  15

Gly Ser Ala His Gln Gly Cys Leu Pro Pro Phe Pro Ala Asp Val Phe
            20                  25                  30

Met Ile Pro Gln Tyr Gly Tyr Leu Thr Leu Asn Asn Gly Ser Gln
        35                  40                  45

<210> SEQ ID NO 2
<211> LENGTH: 47
<212> TYPE: PRT
<213> ORGANISM: Artificial Sequence
<220> FEATURE:
<223> OTHER INFORMATION: Synthetic Sequence

<400> SEQUENCE: 2

Thr Val Gln Val Phe Thr Asp Ser Glu Tyr Gln Leu Pro Tyr Val Leu
1               5                   10                  15

Gly Ser Ala His Gln Gly Cys Leu Pro Pro Phe Pro Ala Asp Val Phe
            20                  25                  30

Met Val Pro Gln Tyr Gly Tyr Leu Thr Leu Asn Asn Gly Ser Gln
        35                  40                  45

<210> SEQ ID NO 3
<211> LENGTH: 47
<212> TYPE: PRT
<213> ORGANISM: Artificial Sequence
<220> FEATURE:
<223> OTHER INFORMATION: Synthetic Sequence
```

```
<400> SEQUENCE: 3

Thr Val Gln Val Phe Thr Asp Ser Glu Tyr Gln Leu Pro Tyr Val Leu
 1               5                  10                  15

Gly Ser Ala His Gln Gly Cys Leu Pro Pro Phe Pro Ala Asp Val Phe
             20                  25                  30

Met Val Pro Gln Tyr Gly Tyr Leu Thr Leu Asn Asn Gly Ser Gln
         35                  40                  45

<210> SEQ ID NO 4
<211> LENGTH: 47
<212> TYPE: PRT
<213> ORGANISM: Artificial Sequence
<220> FEATURE:
<223> OTHER INFORMATION: Synthetic Sequence

<400> SEQUENCE: 4

Thr Val Gln Val Phe Thr Asp Ser Glu Tyr Gln Leu Pro Tyr Val Leu
 1               5                  10                  15

Gly Ser Ala His Gln Gly Cys Leu Pro Pro Phe Pro Ala Asp Val Phe
             20                  25                  30

Met Val Pro Gln Tyr Gly Tyr Leu Thr Leu Asn Asn Gly Ser Gln
         35                  40                  45

<210> SEQ ID NO 5
<211> LENGTH: 50
<212> TYPE: PRT
<213> ORGANISM: Artificial Sequence
<220> FEATURE:
<223> OTHER INFORMATION: Synthetic Sequence

<400> SEQUENCE: 5

Thr Val Gln Ile Phe Ala Asp Ser Ser Tyr Glu Leu Pro Tyr Val Met
 1               5                  10                  15

Asp Ala Gly Gln Glu Gly Ser Leu Pro Pro Phe Pro Asn Asp Val Phe
             20                  25                  30

Met Val Pro Gln Tyr Gly Tyr Cys Gly Leu Val Thr Gly Asn Thr Ser
         35                  40                  45
Gln Gln
     50

<210> SEQ ID NO 6
<211> LENGTH: 49
<212> TYPE: PRT
<213> ORGANISM: Artificial Sequence
<220> FEATURE:
<223> OTHER INFORMATION: Synthetic Sequence

<400> SEQUENCE: 6

Thr Val Gln Val Phe Thr Asp Asp Tyr Gln Leu Pro Tyr Val Val
 1               5                  10                  15

Gly Asn Gly Thr Glu Gly Cys Leu Pro Ala Phe Pro Pro Gln Val Phe
             20                  25                  30

Thr Leu Pro Gln Tyr Gly Tyr Ala Thr Leu Asn Arg Asp Asn Thr Glu
         35                  40                  45
Asn

<210> SEQ ID NO 7
<211> LENGTH: 47
<212> TYPE: PRT
<213> ORGANISM: Artificial Sequence
<220> FEATURE:
```

<223> OTHER INFORMATION: Synthetic Sequence

<400> SEQUENCE: 7

Thr Val Gln Val Phe Ser Asp Ser Glu Tyr Gln Leu Pro Tyr Val Leu
1               5                   10                  15
Gly Ser Ala His Gln Gly Cys Leu Pro Pro Phe Pro Ala Asp Val Phe
            20                  25                  30
Met Ile Pro Gln Tyr Gly Tyr Leu Thr Leu Asn Asn Gly Ser Gln
        35                  40                  45

<210> SEQ ID NO 8
<211> LENGTH: 47
<212> TYPE: PRT
<213> ORGANISM: Artificial Sequence
<220> FEATURE:
<223> OTHER INFORMATION: Synthetic Sequence

<400> SEQUENCE: 8

Thr Ile Gln Val Phe Ser Asp Ser Glu Tyr Gln Leu Pro Tyr Val Leu
1               5                   10                  15
Gly Ser Ala His Gln Gly Cys Leu Pro Pro Phe Pro Ala Asp Val Phe
            20                  25                  30
Met Ile Pro Gln Tyr Gly Tyr Leu Thr Leu Asn Asn Gly Ser Gln
        35                  40                  45

<210> SEQ ID NO 9
<211> LENGTH: 47
<212> TYPE: PRT
<213> ORGANISM: Artificial Sequence
<220> FEATURE:
<223> OTHER INFORMATION: Synthetic Sequence

<400> SEQUENCE: 9

Thr Ile Gln Val Phe Thr Asp Ser Glu Tyr Gln Leu Pro Tyr Val Leu
1               5                   10                  15
Gly Ser Ala His Gln Gly Cys Leu Pro Pro Phe Pro Ala Asp Val Phe
            20                  25                  30
Met Ile Pro Gln Tyr Gly Tyr Leu Thr Leu Asn Asn Gly Ser Gln
        35                  40                  45

<210> SEQ ID NO 10
<211> LENGTH: 50
<212> TYPE: PRT
<213> ORGANISM: Artificial Sequence
<220> FEATURE:
<223> OTHER INFORMATION: Synthetic Sequence

<400> SEQUENCE: 10

Ala Val Gly Arg Ser Ser Phe Tyr Cys Leu Glu Tyr Phe Pro Ser Gln
1               5                   10                  15
Met Leu Arg Thr Gly Asn Asn Phe Thr Phe Ser Tyr Thr Phe Glu Glu
            20                  25                  30
Val Pro Phe His Ser Ser Tyr Ala His Ser Gln Ser Leu Asp Arg Leu
        35                  40                  45
Met Asn
    50

<210> SEQ ID NO 11
<211> LENGTH: 50
<212> TYPE: PRT
<213> ORGANISM: Artificial Sequence
<220> FEATURE:

<223> OTHER INFORMATION: Synthetic Sequence

<400> SEQUENCE: 11

Ala Val Gly Arg Ser Ser Phe Tyr Cys Leu Glu Tyr Phe Pro Ser Gln
1               5                   10                  15

Met Leu Arg Thr Gly Asn Asn Phe Thr Phe Ser Tyr Thr Phe Glu Asp
            20                  25                  30

Val Pro Phe His Ser Ser Tyr Ala His Ser Gln Ser Leu Asp Arg Leu
        35                  40                  45

Met Asn
    50

<210> SEQ ID NO 12
<211> LENGTH: 50
<212> TYPE: PRT
<213> ORGANISM: Artificial Sequence
<220> FEATURE:
<223> OTHER INFORMATION: Synthetic Sequence

<400> SEQUENCE: 12

Ala Val Gly Arg Ser Ser Phe Tyr Cys Leu Glu Tyr Phe Pro Ser Gln
1               5                   10                  15

Met Leu Arg Thr Gly Asn Asn Phe Gln Phe Ser Tyr Thr Phe Glu Asp
            20                  25                  30

Val Pro Phe His Ser Ser Tyr Ala His Ser Gln Ser Leu Asp Arg Leu
        35                  40                  45

Met Asn
    50

<210> SEQ ID NO 13
<211> LENGTH: 50
<212> TYPE: PRT
<213> ORGANISM: Artificial Sequence
<220> FEATURE:
<223> OTHER INFORMATION: Synthetic Sequence

<400> SEQUENCE: 13

Ala Val Gly Arg Ser Ser Phe Tyr Cys Leu Glu Tyr Phe Pro Ser Gln
1               5                   10                  15

Met Leu Arg Thr Gly Asn Asn Phe Gln Phe Ser Tyr Thr Phe Glu Asp
            20                  25                  30

Val Pro Phe His Ser Ser Tyr Ala His Ser Gln Ser Leu Asp Arg Leu
        35                  40                  45

Met Asn
    50

<210> SEQ ID NO 14
<211> LENGTH: 50
<212> TYPE: PRT
<213> ORGANISM: Artificial Sequence
<220> FEATURE:
<223> OTHER INFORMATION: Synthetic Sequence

<400> SEQUENCE: 14

Gln Thr Asp Arg Asn Ala Phe Tyr Cys Leu Glu Tyr Phe Pro Ser Gln
1               5                   10                  15

Met Leu Arg Thr Gly Asn Asn Phe Glu Ile Thr Tyr Ser Phe Glu Lys
            20                  25                  30

Val Pro Phe His Ser Met Tyr Ala His Ser Gln Ser Leu Asp Arg Leu
        35                  40                  45

```
Met Asn
    50

<210> SEQ ID NO 15
<211> LENGTH: 50
<212> TYPE: PRT
<213> ORGANISM: Artificial Sequence
<220> FEATURE:
<223> OTHER INFORMATION: Synthetic Sequence

<400> SEQUENCE: 15

Pro Thr Glu Arg Ser Ser Phe Phe Cys Leu Glu Tyr Phe Pro Ser Lys
1               5                   10                  15

Met Leu Arg Thr Gly Asn Asn Phe Glu Phe Thr Tyr Asn Phe Glu Glu
            20                  25                  30

Val Pro Phe His Ser Ser Phe Ala Pro Ser Gln Asn Leu Phe Lys Leu
        35                  40                  45

Ala Asn
    50

<210> SEQ ID NO 16
<211> LENGTH: 50
<212> TYPE: PRT
<213> ORGANISM: Artificial Sequence
<220> FEATURE:
<223> OTHER INFORMATION: Synthetic Sequence

<400> SEQUENCE: 16

Ala Val Gly Arg Ser Ser Phe Tyr Cys Leu Glu Tyr Phe Pro Ser Gln
1               5                   10                  15

Met Leu Arg Thr Gly Asn Asn Phe Thr Phe Ser Tyr Thr Phe Glu Asp
            20                  25                  30

Val Pro Phe His Ser Ser Tyr Ala His Ser Gln Ser Leu Asp Arg Leu
        35                  40                  45

Met Asn
    50

<210> SEQ ID NO 17
<211> LENGTH: 50
<212> TYPE: PRT
<213> ORGANISM: Artificial Sequence
<220> FEATURE:
<223> OTHER INFORMATION: Synthetic Sequence

<400> SEQUENCE: 17

Ser Val Gly Arg Ser Ser Phe Tyr Cys Leu Glu Tyr Phe Pro Ser Gln
1               5                   10                  15

Met Leu Arg Thr Gly Asn Asn Phe Glu Phe Ser Tyr Ser Phe Glu Asp
            20                  25                  30

Val Pro Phe His Ser Ser Tyr Ala His Ser Gln Ser Leu Asp Arg Leu
        35                  40                  45

Met Asn
    50

<210> SEQ ID NO 18
<211> LENGTH: 50
<212> TYPE: PRT
<213> ORGANISM: Artificial Sequence
<220> FEATURE:
<223> OTHER INFORMATION: Synthetic Sequence

<400> SEQUENCE: 18
```

```
Ala Val Gly Arg Ser Ser Phe Tyr Cys Leu Glu Tyr Phe Pro Ser Gln
 1               5                  10                  15

Met Leu Arg Thr Gly Asn Asn Phe Gln Phe Thr Tyr Thr Phe Glu Asp
            20                  25                  30

Val Pro Phe His Ser Ser Tyr Ala His Ser Gln Ser Leu Asp Arg Leu
            35                  40                  45

Met Asn
    50

<210> SEQ ID NO 19
<211> LENGTH: 414
<212> TYPE: DNA
<213> ORGANISM: Homo Sapiens

<400> SEQUENCE: 19
atggaaactc tcctgggagt gtctttggtg attctatggc ttcaactggc tagggtgaac      60
agtcaacagg gagaagagga tcctcaggcc ttgagcatcc aggagggtga aaatgccacc     120
atgaactgca gttacaaaac tagtataaac aatttacagt ggtatagaca aaattcaggt     180
agaggccttg tccacctaat tttaatacgt tcaaatgaaa gagagaaaca cagtggaaga     240
ttaagagtca cgcttgacac ttccaagaaa agcagttcct tgttgatcac ggcttcccgg     300
gcagcagaca ctgcttctta cttctgtgct acggaccccc cgtacaataa caatgacatg     360
cgctttggag cagggaccag actgacagta aaaccaaata tccagaaccc tgac           414

<210> SEQ ID NO 20
<211> LENGTH: 405
<212> TYPE: DNA
<213> ORGANISM: Homo Sapiens

<400> SEQUENCE: 20
atggaaactc tcctgggagt gtctttggtg attctatggc ttcaactggc tagggtgaac      60
agtcaacagg gagaagagga tcctcaggcc ttgagcatcc aggagggtga aaatgccacc     120
atgaactgca gttacaaaac tagtataaac aatttacagt ggtatagaca aaattcaggt     180
agaggccttg tccacctaat tttaatacgt tcaaatgaaa gagagaaaca cagtggaaga     240
ttaagagtca cgcttgacac ttccaagaaa agcagttcct tgttgatcac ggcttcccgg     300
gcagcagaca ctgcttctta cttctgtgct acgctttaca tgccagact catgtttgga     360 gatggaactc agctggtggt gaagccaaat atccagaacc ctgac                     405

<210> SEQ ID NO 21
<211> LENGTH: 393
<212> TYPE: DNA
<213> ORGANISM: Homo Sapiens

<400> SEQUENCE: 21
atgagcctcg ggctcctgtg ctgtggggtc ttttctctcc tgtgggcagg tccagtgaat      60
gctggtgtca ctcagacccc aaaattccgg gtcctgaaga caggacagag catgacactg     120
ctgtgtgccc aggatatgaa ccatgaatac atgtactggt atcgacaaga cccaggcatg     180
gggctgaggc tgattcatta ctcagttggt gagggtacaa ctgccaaagg agaggtccct     240
gatggctaca atgtctccag attaaaaaaa cagaatttcc tgctggggtt ggagtcggct     300
gctccctccc aaacatctgt gtacttctgt gccagcaggt ccgggtcggc gggagctttc     360
tttggacaag gcaccagact cacagttgta gag                                  393
```

```
<210> SEQ ID NO 22
<211> LENGTH: 405
<212> TYPE: DNA
<213> ORGANISM: Homo Sapiens

<400> SEQUENCE: 22
atggtcctga aattctccgt gtccattctt tggattcagt tggcatgggt gagcacccag    60
ctgctggagc agagccctca gtttctaagc atccaagagg gagaaaatct cactgtgtac   120
tgcaactcct caagtgtttt ttccagctta caatggtaca gacaggagcc tggggaaggt   180
cctgtcctcc tggtgacagt agttacgggt ggagaagtga agaagctgaa gagactaacc   240
tttcagtttg gtgatgcaag aaaggacagt tctctccaca tcactgcggc ccagcctggt   300
gatacaggcc tctacctctg tgcagggaag aagactaacg actacaagct cagctttgga   360
gccggaacca cagtaactgt aagagcaaat atccagaacc ctgac                   405

<210> SEQ ID NO 23
<211> LENGTH: 404
<212> TYPE: DNA
<213> ORGANISM: Homo Sapiens

<400> SEQUENCE: 23
atgggctgca ggctgctctg ctgtgcggtt ctctgtctcc tgggagcggt ccccatggaa    60
acgggagtta cgcagacacc aagacacctg gtcatgggaa tgacaaataa ggagtctttg   120
aaatgtgaac aacatctggg tcataacgct atgtattggt acaagcaaag tgctaagaag   180
ccactggagc tcatgtttgt ctacagtctt gaagaacggg ttgaaaacaa cagtgtgcca   240
agtcgcttct cacctgaatg ccccaacagc tctcacttat tccttcacct acacaccctg   300
cagccagaag actcggccct gtatctctgc gccagcagcc aggacagggt aaacttggcg   360
ggagagcagt acttcgggcc gggcaccagg ctcacggtca caga                    404

<210> SEQ ID NO 24
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 24

Ala Gly Asp Asn Pro Tyr Leu Arg Tyr
 1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 25

Lys Thr Asp Asn Asn Asn Ser Asn Phe
 1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 26
```

Ser Asn Asp Asn His Tyr Phe Gly Tyr
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 27

Ser Gly Asp Asn Pro Tyr Leu Lys Tyr
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 28

Ser Ala Asp Asn Asn Asn Ser Glu Tyr
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 29

Gln Leu Asp Ser Gly Asp Asn Pro Tyr
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 30

Ala Gly Asp Asn Pro Tyr Leu Arg Tyr
1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 31

Thr Asn Asp Asn Thr Tyr Phe Gly Tyr
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 32

Arg Ser Ser Phe Tyr Cys Leu Glu Tyr

```
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 33

Leu Ile Asp Gln Tyr Leu Tyr Tyr Leu
1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 34

Cys Leu Pro Pro Phe Pro Ala Asp Val
1               5

<210> SEQ ID NO 35
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 35

Thr Leu Asn Asn Gly Ser Gln Ala Val
1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 36

Leu Ile Asp Gln Tyr Leu Tyr Tyr Leu
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 37

Cys Leu Pro Pro Phe Pro Ala Asp Val
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 38

Thr Leu Asn Asn Gly Ser Gln Ala Val
1               5
```

<210> SEQ ID NO 39
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 39

Leu Ile Asp Gln Tyr Leu Tyr Tyr Leu
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 40

Cys Leu Pro Pro Phe Pro Ala Asp Val
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 41

Thr Leu Asn Asn Gly Ser Gln Ala Val
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 42

Pro Leu Met Gly Gly Phe Gly Leu Lys
1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 43

Val Leu Glu Pro Leu Gly Leu Val Glu
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 44

Gln Leu Lys Ala Gly Asp Asn Pro Tyr
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 45

Pro Leu Met Gly Gly Phe Gly Leu Lys
 1               5

<210> SEQ ID NO 46
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 46

Val Leu Glu Pro Leu Gly Leu Val Glu
 1               5

<210> SEQ ID NO 47
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 47

Pro Val Lys Thr Ala Pro Gly Lys Lys
 1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 48

Pro Leu Met Gly Gly Phe Gly Leu Lys
 1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 49

Gly Ile Arg Glu Trp Trp Ala Leu Lys
 1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 50

Glu Val Thr Gln Asn Glu Gly Thr Lys
 1               5

```
<210> SEQ ID NO 51
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 51

Ile Pro Gln Tyr Gly Tyr Leu Thr Leu
 1               5

<210> SEQ ID NO 52
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 52

Phe Pro Met Ser Gly Val Met Ile Phe
 1               5

<210> SEQ ID NO 53
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 53

Gln Pro Ala Lys Lys Arg Leu Asn Phe
 1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 54

Val Pro Gln Tyr Gly Tyr Leu Thr Leu
 1               5

<210> SEQ ID NO 55
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 55

Ala Pro Ser Gly Leu Gly Thr Asn Thr
 1               5

<210> SEQ ID NO 56
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 56

Val Pro Ala Asn Pro Ser Thr Thr Phe
 1               5

<210> SEQ ID NO 57
```

```
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 57

Ile Pro Gln Tyr Gly Tyr Leu Thr Leu
1               5

<210> SEQ ID NO 58
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 58

Ala Pro Ser Gly Val Gly Pro Asn Thr
1               5

<210> SEQ ID NO 59
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 59

Lys Pro Gly Ala Pro Lys Pro Lys Ala
1               5

<210> SEQ ID NO 60
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 60

Thr Thr Ser Thr Arg Thr Trp Ala Leu
1               5

<210> SEQ ID NO 61
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 61

Arg Pro Lys Arg Leu Asn Phe Lys Leu
1               5

<210> SEQ ID NO 62
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 62

Gln Ala Lys Lys Arg Val Leu Glu Pro
1               5

<210> SEQ ID NO 63
<211> LENGTH: 9
```

```
<212> TYPE: PRT
<213> ORGANISM: Artificial Sequence
<220> FEATURE:
<223> OTHER INFORMATION: Synthetic Sequence

<400> SEQUENCE: 63

Thr Thr Ser Thr Arg Thr Trp Ala Leu
 1               5

<210> SEQ ID NO 64
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 64

Arg Pro Lys Arg Leu Asn Phe Lys Leu
 1               5

<210> SEQ ID NO 65
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 65

Gln Ala Lys Lys Arg Val Leu Glu Pro
 1               5

<210> SEQ ID NO 66
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 66

Thr Thr Ser Thr Arg Thr Trp Ala Leu
 1               5

<210> SEQ ID NO 67
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 67

Arg Pro Lys Arg Leu Ser Phe Lys Leu
 1               5

<210> SEQ ID NO 68
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 68

Ala Pro Lys Pro Lys Ala Asn Gln Gln
 1               5

<210> SEQ ID NO 69
<211> LENGTH: 9
<212> TYPE: PRT
```

```
<213> ORGANISM: Artificial Sequence
<220> FEATURE:
<223> OTHER INFORMATION: Synthetic Sequence

<400> SEQUENCE: 69

Pro Leu Ile Asp Gln Tyr Leu Tyr Tyr
 1               5

<210> SEQ ID NO 70
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 70

Gln Leu Lys Ala Gly Asp Asn Pro Tyr
 1               5

<210> SEQ ID NO 71
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 71

Pro Leu Ile Asp Gln Tyr Leu Tyr Tyr
 1               5

<210> SEQ ID NO 72
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 72

Tyr His Leu Asn Gly Arg Asp Ser Leu
 1               5

<210> SEQ ID NO 73
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 73

Pro Leu Ile Asp Gln Tyr Leu Tyr Tyr
 1               5

<210> SEQ ID NO 74
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 74

Lys Leu Asn Ser Phe Ile Thr Gln Tyr
 1               5

<210> SEQ ID NO 75
<211> LENGTH: 9
<212> TYPE: PRT
<213> ORGANISM: Artificial Sequence
```

```
<220> FEATURE:
<223> OTHER INFORMATION: Synthetic Sequence

<400> SEQUENCE: 75

Pro Glu Val Gln Tyr Thr Ser Asn Tyr
 1               5

<210> SEQ ID NO 76
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 76

Ser Glu Tyr Gln Leu Pro Tyr Val Leu
 1               5

<210> SEQ ID NO 77
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 77

Pro Glu Ile Gln Tyr Thr Ser Asn Tyr
 1               5

<210> SEQ ID NO 78
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 78

Ser Glu Tyr Gln Leu Pro Tyr Val Leu
 1               5

<210> SEQ ID NO 79
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 79

Pro Glu Ile Gln Tyr Thr Ser Asn Tyr
 1               5

<210> SEQ ID NO 80
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 80

Ser Glu Tyr Gln Leu Pro Tyr Val Leu
 1               5

<210> SEQ ID NO 81
<211> LENGTH: 9
<212> TYPE: PRT
<213> ORGANISM: Artificial Sequence
<220> FEATURE:
```

<223> OTHER INFORMATION: Synthetic Sequence

<400> SEQUENCE: 81

Ile Pro Gln Tyr Gly Tyr Leu Thr Leu
1               5

<210> SEQ ID NO 82
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 82

Val Ala Thr Glu Arg Phe Gly Thr Val
1               5

<210> SEQ ID NO 83
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 83

Phe Pro Met Ser Gly Val Met Ile Phe
1               5

<210> SEQ ID NO 84
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 84

Val Pro Gln Tyr Gly Tyr Leu Thr Leu
1               5

<210> SEQ ID NO 85
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 85

Val Pro Ala Asn Pro Ser Thr Thr Phe
1               5

<210> SEQ ID NO 86
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 86

Phe Pro Gln Ser Gly Val Leu Ile Phe
1               5

<210> SEQ ID NO 87
<211> LENGTH: 9
<212> TYPE: PRT
<213> ORGANISM: Artificial Sequence
<220> FEATURE:
<223> OTHER INFORMATION: Synthetic Sequence

```
<400> SEQUENCE: 87

Ile Pro Gln Tyr Gly Tyr Leu Thr Leu
1               5

<210> SEQ ID NO 88
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 88

Ile Ala Asn Asn Leu Thr Ser Thr Ile
1               5

<210> SEQ ID NO 89
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 89

Thr Ala Pro Gly Lys Lys Arg Pro Val
1               5
```